United States Patent [19]

Gerlach

[11] 4,205,226
[45] May 27, 1980

[54] AUGER ELECTRON SPECTROSCOPY

[75] Inventor: Robert Gerlach, Minnetonka, Minn.

[73] Assignee: Perkin-Elmer Corporation, Norwalk, Conn.

[21] Appl. No.: 938,842

[22] Filed: Sep. 1, 1978

[51] Int. Cl.² .......................................... H01J 39/00
[52] U.S. Cl. ..................................... 250/305; 250/310
[58] Field of Search .............. 250/305, 309, 310, 511, 250/513, 514, 397, 398

[56] References Cited

U.S. PATENT DOCUMENTS

| | | | |
|---|---|---|---|
| 3,102,194 | 8/1963 | Broek et al. | 250/514 |
| 3,774,042 | 11/1973 | Engel | 250/514 |
| 3,845,305 | 10/1974 | Liebl | 250/310 |
| 3,920,990 | 11/1975 | Nieuwland et al. | 250/310 |
| 4,048,498 | 9/1977 | Gerlach et al. | 250/305 |
| 4,100,409 | 7/1978 | Brongersma | 250/305 |
| 4,107,526 | 8/1978 | McKinney et al. | 250/305 |

Primary Examiner—Bruce C. Anderson
Attorney, Agent, or Firm—Schroeder, Siegfried, Ryan, Vidas, Steffey & Arrett

[57] ABSTRACT

An instrument utilizing the Auger effect and including a cylindrical mirror analyzer with magnetic lenses and an off-axis annular-aperture collector apparatus arranged in a unique configuration.

38 Claims, 6 Drawing Figures

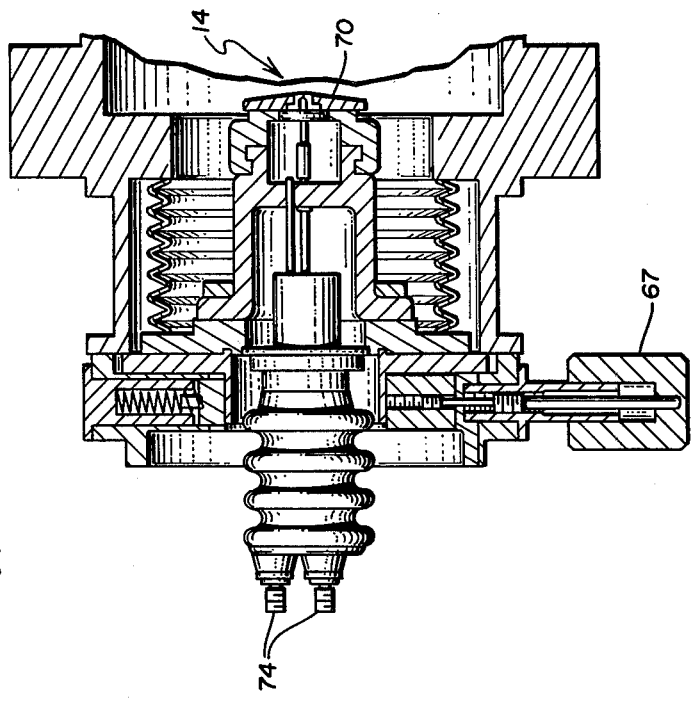
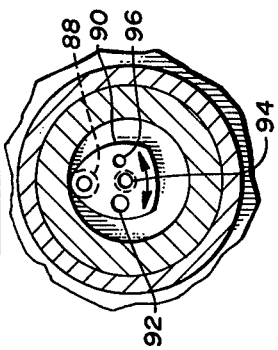
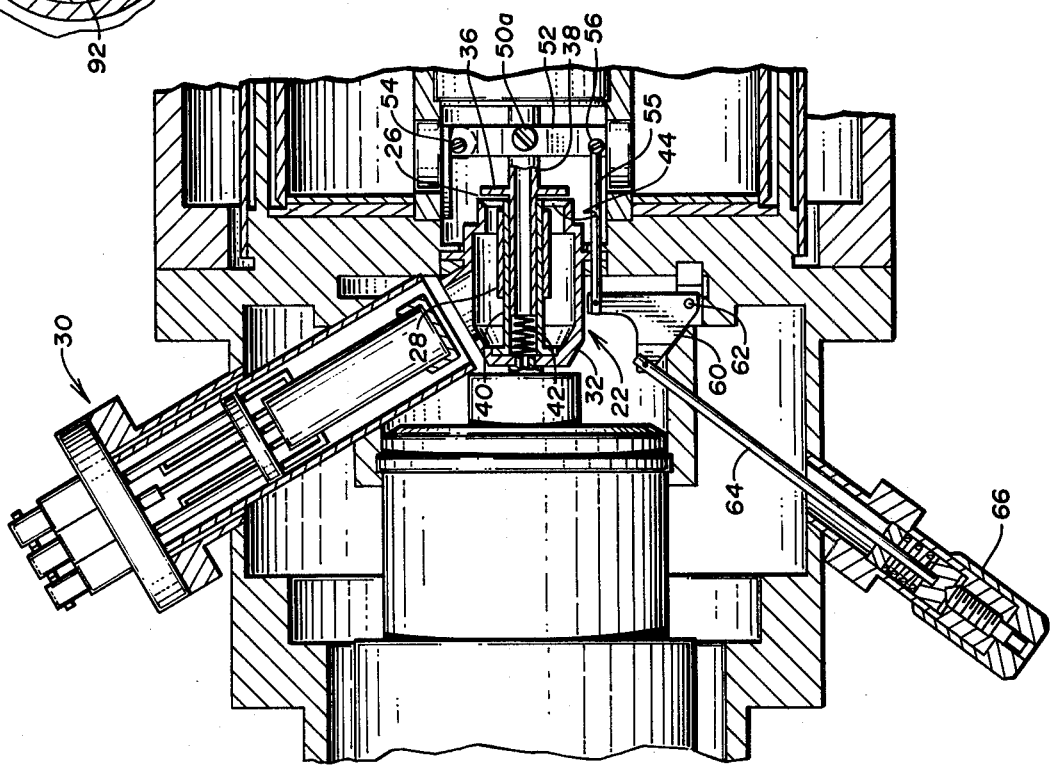

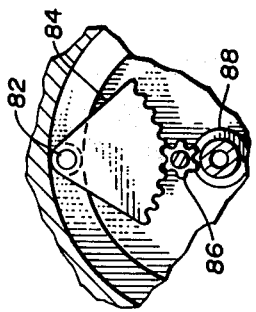
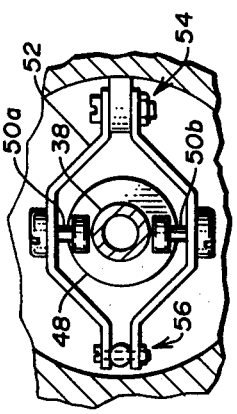
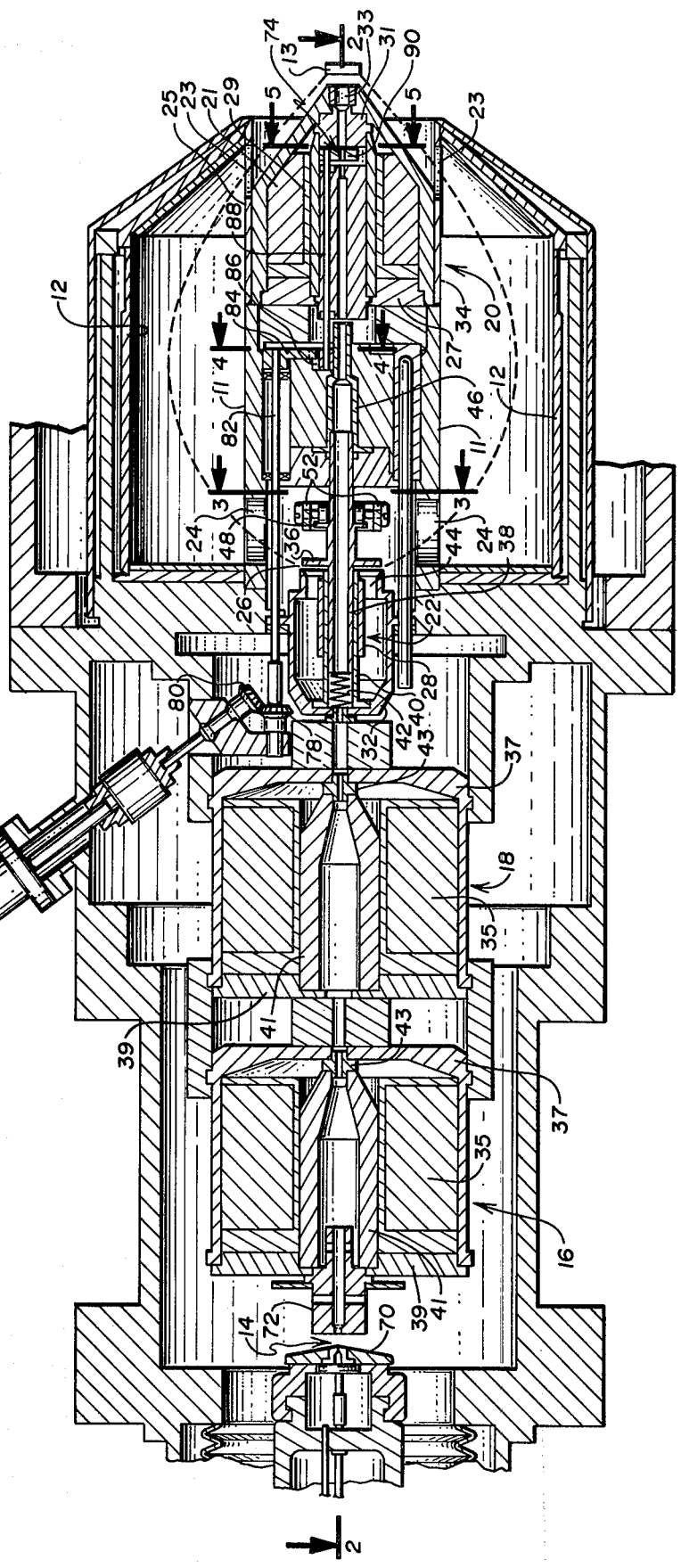

AUGER ELECTRON SPECTROSCOPY

BACKGROUND OF INVENTION

This invention relates to charged particle spectroscopy and particularly, although not exclusively, to an improved instrument and components for use in electron spectroscopy, specifically Auger electron spectroscopy.

Instrumentation for use in electron spectroscopy makes use of electrons which are emitted from a substance after being bombarded or irradiated with electrons from a source such as an electron gun. The technique to which the invention is specifically directed is to one known as Auger electron spectroscopy. In this type of a technique, a target sample material is placed in a vacuum, usually below about $10^{-7}$ Torr, and upon being bombarded with electrons from some source, such as an electron gun, the sample gives off a variety of emissions. Among these are X-rays, secondary electrons, and reflected primary electrons from the source. The sample gives off Auger electrons (a particular class of secondary electrons) in the manner which is well known in the literature.

In the art of Auger electron spectroscopy, instruments making use of cylindrical mirror analyzers are known which analyze the energy and the energy spectrum of Auger electrons emitted by the sample material by injecting the electrons into a radial electric field produced between a pair of coaxially mounted electrodes held at different electric potentials. Auger electrons injected into the radial electric field between the cylindrical electrodes are deflected by the field toward the common axis of the electrodes. Electrons of a predetermined energy are thereby brought to a focus. By positioning a collector apparatus at this focus, electrons of a predetermined energy are selected and detected. By sweeping the voltage impressed across the cylindrical electrodes through a range of values, and detecting as a function of these applied potentials such electrons as are collected, the energy spectrum of the injected electrons may be plotted and determined.

Prior art instruments incorporate a collector which collects only those electrons which pass close to the analyzer axis. Consequently, any magnetic field or the like which deflects the paths of such electrons reduces the likelihood of their collection. This has prevented the use of coaxial magnetic lenses and the like in these instruments in the past since such lenses affect the electron's path.

SUMMARY OF THE INVENTION

According to the invention, in a spectroscopic instrument making use of a cylindrical mirror analyzer or other analyzer types, the various components of the instrument are arranged in a new and novel manner and certain of the components themselves are of a new and novel design.

In the new configuration of the invention, a novel off-axis collector apparatus or charged particle detecting means is used in conjunction with an objective lens. It is preferred that the objective lens be a magnetic objective lens. Both components, the collector and objective lens, are located at least partially within the cylindrical mirror analyzer portion of the instrument and near opposite ends thereof.

The novel off-axis collector apparatus includes a variable or adjustable off-axis annular aperture. The off-axis collector arrangement of the invention is particularly designed to alleviate the problem caused by the influence of extraneous, cylindrically symmetrical magnetic field effects and the like on the paths of the changed particles. Magnetic lenses, for example, are sources of such effects. The off-axis collector assures the collection of charged particles which have been displaced off-axis by such effects. This is of particular importance when the charged particles are electrons and the continued discussion hereinbelow is in that context, specifically Auger electrons.

As previously mentioned, the annular aperture of the collector apparatus is designed to be continuously adjustable in gap width. The basic advantage of the annular off-axis aperture is that it is relatively insensitive to magnetic fields, particularly those provided by a magnetic objective lens. To first approximation, the same total current in a peak is transmitted in spite of the presence of a magnetic field with this geometry. In addition, the analyzer resolution is not degraded to first order approximation by cylindrically symmetric magnetic fields. Furthermore, the annular aperture has a larger useful working area in front of the cylindrical analyzer, that is, the Auger peaks will not fall off as rapidly with beam deflection, especially for low energy Auger peaks.

The arrangement of components as provided herein has a number of advantages. For example, only the objective lens and deflection system of the instrument need be inside the analyzer. The remainder of the instrument components, such as condenser lenses and electron gun can be located behind the cylindrical mirror analyzer section of the instrument. Placing the condenser lenses behind the cylindrical analyzer reduces the magnetic field inside the cylindrical analyzer. It also allows for additional space and for longer focal lengths in the instrument. Placing the electron source or electron gun toward the rear of the instrument makes the filament thereof readily accessible for replacement. This allows operators the choice of burning the filaments at higher temperatures to obtain increased brightness. Such operation requires more frequent filament replacement, but with the instant configuration, filament replacement is made more convenient than has been theretofore provided by instruments in this art.

Various additional advantages and other features of the invention will become clear upon review of the accompanying description and drawings.

BRIEF DESCRIPTION OF THE DRAWINGS

FIG. 1 (in two sections 1a and 1b) is a longitudinal cross-section of an instrument of the cylindrical mirror Auger type incorporating a magnetically shielded magnetic objective lens, an off-axis, variable aperture, electron collector apparatus, the instrument having the various components thereof arranged in novel configuration according to the invention;

FIG. 2 is a cross-sectional view taken along line 2—2 of FIG. 1 which lies along the central axis of the instrument. The view of FIG. 2 is only of a central portion of the instrument and does not include either of the end portions thereof;

FIG. 3 is a cross-sectional view taken along 3—3 of FIG. 1;

FIG. 4 is a cross-sectional view taken along line 4—4 of FIG. 1, and

FIG. 5 is a cross-sectional view taken along line 5—5 of FIG. 1.

DESCRIPTION OF PREFERRED EMBODIMENT

Referring to FIG. 1, as already indicated, the preferred embodiment takes the form of an Auger spectrometer. The instrument as shown includes a pair of coaxial cylindrical metal electrodes 11 and 12. Electrodes 11 and 12 are mutually electrically insulated so that, in operation, the outer electrode 12 can be held at a different potential with respect to the inner electrode 11, thus providing a radially directed electric field in the space between the electrodes 11 and 12, thereby providing means defining a path for charged particles between the cylinders. Preferably, inner electrode 11 is grounded. A target specimen or test sample 13, indicated schematically, is mounted as shown on the common axis 2—2 which is the central axis of the instrument and the common axis along which other components thereof are spacedly positioned.

In operation of the coaxial analyzer apparatus of the instrument, test sample 13 is bombarded or irradiated with a beam of electrons from an electron source, generally indicated at 14, so as to cause test sample 13 to emit Auger electrons. The energies of the electrons emitted by specimen 13 will depend on the chemical structure of the sample and on the nature of the bombarding electrons. The irradiating beam of electrons originating at source 14 proceeds axially through the instrument along axis 2—2 to specimen 13. As the electrons move through the instrument toward specimen 13 from source 14, they pass through electromagnetic condenser lenses generally indicated at 16 and 18 and through an electromagnetic objective lens generally indicated at 20. The irradiating electrons also pass through the center of a collector apparatus, generally indicated at 22, which is axially positioned about axis 2—2 to allow passage of the stream of electrons therethrough. Various other components of the instrument which are axially positioned about axis 2—2, are also designed and arranged to allow for the passage of the stream of irradiating electrons therethrough as can be seen in the drawings.

Auger electrons emitted by test sample 13 follow the path between cylinders 11 and 12 indicated by the dotted lines through the analyzer section of the instrument. The electrons pass through annular aperture 23, which in this case is formed in inner electrode 11 but may be formed in a separate member, aperture 23 serving to allow the entrance of the emitted Auger electrons into the area between inner cylinder 11 and outer cylinder 12 of the coaxial analyzer section of the instrument. Auger electrons passing through aperture 23 enter the radial electric field between electrodes 11 and 12 and are deflected by the field toward the axis 2—2 of the analyzer and the instrument. The deflected electrons pass through an annular exit aperture 24 in inner electrode 11. Preferably, the apertures are covered with a metallic gauze or mesh as is known in the art. The electron optics of a coaxial analyzer, also referred to as cylindrical mirror analyzer, are such that electrons of a predetermined energy, depending upon the strength of the radial electric field, and traveling in radial planes with respect to the analyzer, are brought to a focus at the off-axis annular entrance aperture 26 defined by the electron detecting means or collector apparatus 22. Electrons passing through this aperture enter collector apparatus 22 and the apparatus produces an output signal proportional to the rate at which it receives the electrons. Apparatus 22 includes the first dynode 28 of an electron multiplier, generally indicated at 30, as seen in FIG. 2, which is operatively connected with apparatus 22 in the standard way as is typically known in the art. In this arrangement, first dynode or detecting band 28, a material eg., berylium-copper, which is responsive to the charged particles, is located within housing 32 of collecting apparatus 22 such that it is disposed to receive by impingement any electrons entering aperture 26. The material emits additional electrons in response to such impingement thus amplifying the flow of charged particles. Other configurations, such as a channel plate multiplier, may be used in place of band 28.

Magnetic lenses 16, 18, and 20 are of types known in the art. Objective lens 20 comprises an electromagnetic coil 21 and a magnetic shield 25, 27, and 29. The magnetic flux generated by coil 21 localizes at magnetic gap 31 to focus the irradiating beam of charged particles passing through the lens on target 13. Magnetic gap 31 consists of a body of non-magnetic material such as molybdenum. The lens includes a set of electrostatic deflection plates 33 which scan the beam of irradiating particles on the test sample 13.

Condenser lenses 16 and 18 are of a construction generally similar to objective lens 20 and include a coil 35, shield 37, 39, and 41, and a magnetic gap body 43. The lenses function to condense the beam of irradiating particles. Lenses of this general type 16, 18 and 20 are shown in *Electron Optics*, by P. Grivet, Pergamon Press, New York, 1965, at pages 231 and 475.

As previously indicated, electron detecting means or collector apparatus 22 is an off-axis collector, ie., dynode 28 is disposed about the axis 2—2 of the instrument inside electron detector housing 32. Furthermore, housing 32 is provided with an annular aperture 26 as previously pointed out for admitting emitted electrons thereinto. The width or size of annular gap 26 is variable and it can be closed or opened to various sizes by means of an end covering means or end cap 36 carried by hollow stem 38 which is reciprocably received within the coaxial bore of axially positioned support 40 in housing 32. A spring 42 in housing 32 presses against the end of stem 38 thereby urging it outwardly from the open end 44 of housing 32 to provide a normally open annular gap 26. Stem 38 is also reciprocably received at its other end in a cylindrical axially positioned support 46 for support purposes, to prevent electrons from leaking into the collector assembly from the irradiating beam and to allow for slit adjustment. Stem 38 and supports 40 and 46 are, of course, tubular about axis 2—2 to allow for the passage therethrough of electrons passing from source 14 to specimen 13.

Annular camming surface 48 on stem 38 rests against camming pins or bearings 50a and 50b which are carried by yoke 52. Yoke 52 is pivotally attached to the interior of the instrument as shown in FIG. 2 and FIG. 3 generally at 54. The opposite end of yoke 52, generally indicated at 56, is contacted by an actuating means for rotating yoke 52 about pivot 54 and thus moving the camming pins or bearings 50a and 50b axially to urge stem 38 and end cap 36 toward housing 32. As shown in FIG. 2, the actuating means connected yoke 52 at 56 comprises a lever arm or push rod 55 attached to a bell crank 60 which is pivotally mounted to the instrument at 62. Another lever arm or push rod 64 is attached to bell crank 60 as shown. Lever arm or push rod 64 is actuated by a screw mechanism generally indicated at 66 whereby rod or arm 64 may be caused to rotate bell crank 60 to impart axial motion to lever 55, thus actuating yoke 52 on its pivot 54 for adjustment of the position of end cap 36.

Such an arrangement provides for an annular gap 26 which may be adjusted from a closed position to open positions of various sizes. Generally, it would also be possible if desired to fix the position of end cover means 36 and move housing 32 to provide the same effect. Such an arrangement would be considered within the scope of the invention.

Electron source 14 includes a filament assembly 70 of a suitable material, such as tungsten or lanthanum hexaboride, and an anode assembly 72. Pins 74 (seen in FIG. 1a) are connected to the filament and are adapted to be received in a socket to which power for heating the filament is applied as is known in the art. Anode assembly 72 accelerates the electron beam from filament assembly 70 along axis 2—2 of the instrument in the known manner. A micrometer device 67 for alignment adjustment of electron source 14 may also be included.

The instrument also preferably includes a variable axial aperture means generally indicated at 74 (FIG. 1b) in objective lens 20. The variable axial aperture is preferably of the type shown in U.S. Pat. No. 4,048,498 to Gerlach et al dated Sept. 13, 1977, for SCANNING AUGER MICROPROBE WITH VARIABLE AXIAL APERTURE. Specifically, the variable axial aperture means utilized includes a rotary control mechanism 76, as is known in the art, and which is used to rotate a gear 78 by rotation of gear 80 whereby rotatable arm 82 may be used to impart rotation to gear segment 84, (best seen in FIG. 4) and an engaged gear 86, which in turn imparts rotation to rotatable arm 88. Rotatable arm 88 extends into objective lens 20 as shown in FIG. 1b, to interconnect with variable aperture plate 90. Plate 90 contains three apertures of different sizes 92, 94, and 96 (best seen in FIG. 5), each of which may be selectively positioned axially on axis 2—2. For example, such a control mechanism is available from Ultek Inc., a division of Perkin-Elmer, Mountain View, California, as Model No. A-77036.

Having described the preferred embodiment of the invention, the subject matter in which exclusive rights are claimed is defined as follows:

1. In an apparatus for electron spectroscopy, the improvement comprising:
   magnetic lens means for condensing and focusing electrons onto a test sample;
   means defining a housing disposed about the axis of the instrument and adapted for receiving electrons emitted by the sample;
   means defining an off-axis annular gap of adjustable width associated with the housing means in a concentric relationship therewith and with the instrument axis, the means being adapted for admitting emitted electrons through the gap into the housing, and
   electron detector means positioned within the housing proximate the gap for detecting electrons admitted through the gap.

2. Apparatus comprising:
   means for receiving charged particles, the means defining a housing disposed about an axis;
   means for admitting charged particles into the housing, the means defining an annular gap of adjustable width in the housing concentric with the axis thereof;
   means within the housing proximate the gap for detecting charged particles admitted through the gap, and
   wherein the housing has an open end and the means defining the annular gap comprises an end covering means disposed at the open end and actuating means for moving the housing and the end covering means relative to each other for varying the size of the annular gap.

3. Apparatus comprising:
   means for receiving charged particles, the means defining a housing disposed about an axis;
   means for admitting charged particles into the housing, the means defining an annular gap of adjustable width in the housing concentric with the axis thereof;
   means within the housing proximate the gap for detecting charged particles admitted through the gap, and
   wherein the housing has an open end, and the means defining the annular gap comprises an end cap disposed at the open end normal to the axis, and actuating means for moving the end cap toward and away from the open end is included in the apparatus.

4. The apparatus of claim 3 wherein the housing includes an axially positioned support having a coaxial bore therein, and the end cap includes a hollow stem attached thereto and received by the bore for reciprocating motion therein.

5. The apparatus of claim 4 including spring means urging the end cap away from the open end of the housing.

6. The apparatus of claim 4 wherein the charged particle detecting means is disposed on the support.

7. The apparatus of claim 6 wherein the charged particle detecting means is concentrically disposed about the support.

8. The apparatus of claim 7 wherein the charged particle detecting means comprises a band including material responsive to the charged particles.

9. The apparatus of any of the preceding claims 2, 3, 4, 5, 6, 7 or 8 wherein the charged particles are electrons and the detecting means comprises an electron detector.

10. The apparatus of claim 4 wherein the actuating means includes pivotally supported yoke means for urging the end cap to move in a direction along the axis.

11. The apparatus of claim 10 wherein the actuating means further includes linkage means and gear means attached to the yoke means for controlling its position and hence the position of the end cap.

12. The apparatus of claim 5 wherein the actuating means includes a pivotally supported yoke means for urging the end cap toward the housing against the spring means.

13. The apparatus of any of the preceding claims 2, 3, 4, 5, 6, 7, 8, 10, or 12 further including a coaxial cylindrical type analyzer comprising an inner cylinder and an outer cylinder and means defining a path for charged particles through the cylinders and at least that portion of the charged particle receiving housing having the annular gap being disposed coaxially within the end portion of the inner cylinder substantially at the end of the charged particle path defined thereby.

14. Apparatus comprising:
   means for receiving charged particles, the means defining a housing disposed about an axis;

means for admitting charged particles into the housing, the means defining an annular gap of adjustable width in the housing concentric with the axis thereof;

means within the housing proximate the gap for detecting charged particles admitted through the gap, and the apparatus further including a coaxial cylindrical-type analyzer comprising an inner cylinder and an outer cylinder and means defining a path for charged particles through the cylinders and at least that portion of the charged particle receiving housing having the annular gap disposed coaxially within the end portion of the inner cylinder substantially at the end of the charged particle path defined thereby.

15. The apparatus of claim 14 including means for applying voltage between the inner and outer cylinders for controlling the charged particle path.

16. The apparatus of claim 14 including means at the other end of the cylinders for admitting charged particles into the space between the inner and outer cylinders and means at the end portion where the charged particle detecting housing is disposed for admitting the charged particles from the space between the cylinders into the inner cylinder proximate the gap in the charged particle detector housing.

17. The apparatus of any of the preceding claims 15 or 16 wherein the charged particles are electrons and the detecting means comprises an electron detector.

18. An instrument for analyzing the energy of electrons emitted from a test sample, the instrument including a plurality of elements disposed along a common axis and comprising:

source means disposed at one end of the instrument for providing an irradiating beam of electrons along the axis;

an objective lens means disposed at the other end of the instrument for focusing the beam of irradiating electrons onto a test sample to cause the emission of electrons therefrom to be analyzed;

electron detecting means disposed between the source means and the objective lens means for detecting electrons emitted from the test sample, the detecting means defining an axial path therethrough for passage of the beam of irradiating electrons from the source means to the objective lens means and further defining an off-axis annular gap of adjustable width concentric with the axis for admitting the emitted electrons to the detecting means, and means defining a path from the test sample around the objective lens to the detecting means for the emitted electrons.

19. The instrument of claim 18 further including additional lens means disposed between the detecting means and the source means for controlling the irradiating beam of electrons.

20. The instrument of claim 18 wherein the means defining the path between the test sample and the detecting means comprises a coaxial cylindrical type analyzer having at least one inner cylinder and one outer cylinder.

21. The instrument of claim 20 including means for applying the voltage between the inner and outer cylinders for controlling the charged particle path.

22. The instrument of claim 20 wherein the detecting means defines a housing disposed about the instrument axis for receiving emitted electrons from the test sample, and further includes means for admitting emitted electrons into the housing, the means defining an annular gap in the housing concentric about the instrument axis, and means responsive to the electrons within the housing proximate the gap for receiving charged particles admitted through the gap.

23. An instrument for analyzing the energy of charged particles emitted from a test sample, the instrument including a plurality of elements disposed along a common axis and comprising:

source means disposed at one end of the instrument for providing an irradiating beam of charged particles along the axis;

a charged particle objective lens means disposed at the other end of the instrument for focusing the beam of irradiating charged particles onto a test sample to cause the emission of charged particles therefrom to be analyzed;

charged particle detecting means disposed between the source means and the objective lens means including an off-axis annular gap of adjustable width for detecting charged particles emitted from the test sample, the detecting means defining an axial path therethrough for passage of the beam of irradiating charged particles from the source means to the objective lens means, and means defining a path from the test sample to the detecting means for the emitted charged particles.

24. The instrument of claim 23 wherein the means defining the path between the test sample and the detecting means comprises a coaxial cylindrical type analyzer having at least one inner cylinder and one outer cylinder, the detecting means defines a housing disposed about the instrument axis for receiving emitted charged particles from the test sample, and further includes means for admitting emitted charged particles into the housing, the means defining an annular gap in the housing concentric about the instrument axis, and means responsive to the charged particles within the housing proximate the gap for receiving charged particles admitted through the gap, and wherein the housing has an open end and the means defining the annular gap comprises an end cap disposed at the open end normal to the axis, and actuating means for moving the end cap toward and away from the open end is included.

25. The instrument of claim 24 wherein the housing includes an axially positioned support having a coaxial bore therethrough, and the end cap includes a hollow stem attached thereto and a coaxial opening through the end cap at the point of stem attachment, the stem being received by the bore in the support for reciprocating motion therein, the bore and stem and end cap defining a portion of the axial path for the irradiating beam of electrons through the instrument by virtue of the openings therein.

26. The instrument of claim 25 wherein electron responsive means is disposed about the central support in the housing.

27. The instrument of claim 26 wherein electron responsive means comprises the first dynode of a multiplier collector.

28. The instrument of any of the preceding claims 18, 19, 20, 21, 22, 23, 24, 25, 26 or 27 wherein the emitted electrons are Auger electrons.

29. The instrument of claim 18 wherein:
the source means is an electron gun whereby Auger electrons are emitted from the test sample, and
the detecting means includes an electron multiplier.

30. The instrument of any one of the preceding claims 18, 19, 20, 21, 22, 23, 24, 25, 26, 27, or 29 wherein the lens means are electromagnetic.

31. The instrument of any one of the preceding claims 18, 19, 20, 21, 22, 23, 24, 25, 26, 27 or 29 including magnetic shielding disposed about the objective lens.

32. The instrument of claim 25 wherein the actuating means includes pivotally supported yoke means for urging the end cap to move in a direction along the axis.

33. The instrument of claim 32 wherein the actuating means further includes linkage means and gear means actuated by the yoke means for controlling its position and hence the position of the end cap.

34. The instrument of any one of the preceding claims 14, 15, 16, 18, 19, 20, 21, 22, 23, 24, 25, 26, 27, 29, 32 or 33 wherein:
the source means is an electron gun whereby Auger electrons are emitted from the test sample, and
the detecting means includes an electron multiplier.

35. The instrument of any one of the preceding claims 14, 15, 16, 18, 19, 20, 21, 22, 23, 24, 25, 26, 27, 29, 32 or 33 wherein the objective lens means includes variable objective aperture means.

36. In a spectroscopic instrument of the electron charged particle type including a cylindrical mirror analyzer, the improvement comprising in combination a coaxial electron detector means and coaxial magnetic objective lens means, both of which are concentrically disposed about the axis of the instrument and operatively positioned relative to the cylindrical mirror analyzer substantially at opposite ends thereof, the detector means including off-axis electron collector means having an annular, off-axis electron aperture of adjustable width.

37. The instrument of claim 36 wherein the remaining components thereof including the condensor lens means and the electron source means are located to the rear of the cylindrical mirror analyzer portion of the instrument.

38. In a spectroscopic instrument of the electron charged particle type including an electron energy analyzer means, the improvement comprising in combination a coaxial electron detector means and coaxial magnetic objective lens means, both of which are concentrically disposed about the axis of the instrument and operatively positioned relative to the analyzer means substantially at opposite ends thereof, the detector means including off-axis electron collector means having an annular, off-axis electron aperture of adjustable width.

* * * * *